US006446488B1

(12) United States Patent
Kurokawa et al.

(10) Patent No.: US 6,446,488 B1
(45) Date of Patent: *Sep. 10, 2002

(54) GAS CONCENTRATION MEASURING APPARATUS PRODUCING CURRENT SIGNALS AS A FUNCTION OF GAS CONCENTRATION

(75) Inventors: Eiichi Kurokawa, Okazaki; Tomoo Kawase, Nagoya; Satoshi Hada, Kariya; Toshiyuki Suzuki, Handa, all of (JP)

(73) Assignee: Denso Corporation, Kariya (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/321,873

(22) Filed: May 28, 1999

(30) Foreign Application Priority Data

May 29, 1998 (JP) .......................................... 10-150294
Apr. 26, 1999 (JP) .......................................... 11-118083

(51) Int. Cl.[7] ................................................. G01N 7/00
(52) U.S. Cl. ................................. 073/31.05; 073/23.32
(58) Field of Search ........................ 73/23.32; 327/560; 204/425; 205/784.5; 701/103; 330/255

(56) References Cited

U.S. PATENT DOCUMENTS

| 4,718,999 | A | * | 1/1988 | Suzuki et al. ................ 204/406 |
| 4,759,827 | A | * | 7/1988 | Okada et al. ................ 204/1 T |
| 4,915,080 | A | * | 4/1990 | Nakaniwa et al. ........... 123/489 |
| 5,151,166 | A | * | 9/1992 | Harral et al. ................ 204/425 |

(List continued on next page.)

FOREIGN PATENT DOCUMENTS

| DE | 197 28 466 | * | 1/1998 |
| DE | 197 44 439 | * | 4/1998 |
| EP | 0 851 108 | * | 7/1998 |
| GB | 2 290 618 | * | 1/1996 |
| GB | 2 327 270 | * | 1/1999 |

OTHER PUBLICATIONS

Michael Maida and Al Kelsch, "Some insights into rail–to–rail op amp design", May 1999, http://www.computer–design.com/Editorial/1999/04–sup/0499some_insights_in-to.html, pp. 1–3.*

*Primary Examiner*—Hezron Williams
*Assistant Examiner*—C D Garber
(74) *Attorney, Agent, or Firm*—Nixon & Vanderhye P.C.

(57) ABSTRACT

A gas concentration measuring apparatus is provided which may be employed in measuring an air-fuel ratio of mixture sucked into automotive engines. The apparatus includes a gas concentration sensor exposed to a gas and a voltage applying circuit. The gas concentration sensor is responsive to application of voltage to produce a current signal indicative of concentration of the gas. The voltage applying circuit includes an operational amplifier which operates on a source voltage and which outputs the voltage for developing the voltage applied to the gas concentration sensor which has a level changing as a function of voltage inputted to the operational amplifier. The operational amplifier is designed to have an amplitude of each of the voltages inputted to and outputted from the operational amplifier which falls within a given input/output voltage range defined between an upper limit and a lower limit of a source voltage range and near at least one of the upper and lower limits of the source voltage range, thereby allowing the air-fuel ratio to be measured with higher accuracy over a wide range.

13 Claims, 9 Drawing Sheets

U.S. PATENT DOCUMENTS

| | | | | |
|---|---|---|---|---|
| 5,455,535 A | * | 10/1995 | Sauer | 327/560 |
| 5,552,741 A | * | 9/1996 | Kolluri | 327/560 |
| 5,627,486 A | * | 5/1997 | Gross | 327/108 |
| 5,691,464 A | * | 11/1997 | Cao | 73/23.31 |
| 5,777,204 A | * | 7/1998 | Abe | 73/23.32 |
| 5,810,997 A | * | 9/1998 | Okazaki et al. | 205/784.5 |
| 5,833,836 A | * | 11/1998 | Takami et al. | 205/785 |
| 5,852,228 A | * | 12/1998 | Yamashita et al. | 73/23.32 |
| 5,925,088 A | * | 7/1999 | Nasu | 701/103 |
| 5,974,857 A | * | 11/1999 | Yamashita et al. | 73/23.32 |
| 5,980,710 A | * | 11/1999 | Kurokawa et al. | 204/425 |
| 5,993,641 A | * | 11/1999 | Okasaki et al. | 205/784.5 |

* cited by examiner

GAS CONCENTRATION MEASURING APPARATUS PRODUCING CURRENT SIGNALS AS A FUNCTION OF GAS CONCENTRATION

BACKGROUND OF THE INVENTION

1. Technical Field of the Invention

The present invention relates generally to a gas concentration measuring device which may be employed in an air-fuel ratio control system for automotive vehicles to measure a given gas component contained in emissions from an internal combustion engine, more particularly to an improvement on a circuit structure of a gas concentration measuring device equipped with a gas sensor which, when applied with the voltage, produces an electric signal indicative of the concentration of gas.

2. Background Art

Recently, in order to meet requirements for improvement in control accuracy of automotive air-fuel ratio control systems and enhancement of lean burn of internal combustion engines, linear air-fuel ratio sensors designed to measure the concentration of oxygen contained in exhaust gasses of the internal combustion engine to determine the air-fuel ratio of mixture sucked into the engine linearly in a wide range and an air-fuel ratio measuring devices using the same have been proposed. As such air-fuel ratio sensors, a limiting current air-fuel ratio sensor as taught in, for example, U.S. Pat. No. 5,691,464 is known in the art which is responsive to application of voltage to produce a limiting current whose detectable range changes with a change in concentration of oxygen in exhaust gasses.

FIG. 1 shows an air-fuel ratio measuring circuit 80 employed in one example of conventional air-fuel ratio measuring devices.

The air-fuel ratio measuring circuit 80 includes a reference voltage generator 84, amplifying circuits 85 and 86, a current-detecting resistor 88, and a voltage follower 89.

The reference voltage-generator 84 produces a constant reference voltage Va. The reference voltage Va is amplified in current by an operational amplifier 85*a* of the amplifying circuit 85. To one end of an air-fuel ratio sensor 81, the voltage identical with the reference voltage Va is applied. An operational amplifier 86*a* of the amplifying circuit 86 amplifies in current a command voltage Vb produced from a D/A converter 87. The voltage equal to the command voltage Vb is applied to the other end of the air-fuel ratio sensor 81. The command voltage Vb is adjusted by a CPU (not shown) according to an instantaneous air-fuel (A/F) ratio.

The sensor current flows through the air-fuel ratio sensor 81 as a function of the A/F ratio of gases to be measured. A voltage drop across the resistor 88 caused by the flow of the sensor current, that is, a difference between the reference voltage Va and the voltage Vc is monitored by an external electronic control unit (ECU) to determine the value of the A/F ratio. The voltage Vc is inputted to the ECU through the voltage follower 89. The value of the A/F ratio determined in the ECU is employed in the feedback control of the A/F ratio.

FIG. 2 shows a typical circuit structure of each of the operational amplifiers 85*a* and 86*a*. The operational amplifiers 85*a* and 86*a* have the same circuit structure, and explanation below will refer only to the operational amplifier 85*a* for the brevity of disclosure.

The operational amplifier 85*a* operates on a source voltage Vcc of 5 V. An input circuit 91 includes a pair of pnp transistors T21 and T22 which operate on the constant current I1 from a constant current circuit C1 in response to input signals IN+ and IN− to change the collector current as a function of a difference in voltage between the input signals IN+ and IN−. Changes in collector current of the transistors T21 and T22 will activate a pair of npn transistors T23 and T24.

Specifically, when the input signal IN+ is higher in voltage than the input signal IN−, it will cause the collector current of the pnp transistor T22 to increase, so that the collector voltage of the npn transistor T24 is elevated. Alternatively, when the input signal IN+ is lower in voltage than the input signal IN−, it will cause the collector current of the pnp transistor T21 to increase, so that the base current flows in the npn transistors T23 and T24, thereby turning on the npn transistors T23 and T24 so that the collector voltage of the transistor T24 drops.

The collector voltage of the npn transistor T24 is transferred as a signal SG1 to the intermediate amplifying circuit 92. The signal SG1 is amplified and outputted as a signal SG2 to the bias circuit 93. The bias circuit 93 operates on the constant current I2 from the constant current circuit C2 and activates the npn transistor T25 working as a current source or the npn transistor T26 working as a current sink.

When the input signal IN+ is higher in voltage than the input signal IN−, the bias circuit 93 activates the npn transistor T25 to elevate an output voltage. Alternatively, when the input signal N+ is lower in voltage than the input signal IN−, the bias circuit 93 activates the npn transistor T26 to decrease the output voltage.

Each of the operational amplifiers 85*a* and 86*a*, however, has the drawback in that a voltage output is produced only within a range narrower than a range from the source voltage Vcc to ground potential by given voltage losses. Increasing the accuracy in measuring the concentration of gas requires broadening the range of the output voltage.

The reason that the range of the output voltage is limited to be narrower than the range from the source voltage Vcc to ground potential will be discussed below.

The voltage of the input signal IN+ depends upon a voltage drop VI1 across the constant current circuit C1 and the base-emitter voltage VF1 of the transistor T21 (or the base-emitter voltage VF2 of the transistor T22). Specifically, the voltage of the input signal IN− depends upon the voltage drop VI1 and the base-emitter voltage VF2 developed across the transistor T22. The transistors T21 and T22, therefore, operate normally within a voltage range below Vcc−VI1−VF1 (or −VF2). If VF1=VF2=0.7 V and VI1=0.6 V, then a maximum voltage of each of the input signals IN+ and IN− is restricted to 5 V−0.6 V−0.7 V=3.7 V.

The npn transistor T25 operates on the constant current I2 from the constant current circuit C2 and allow the base current to flow. An upper limit of the output voltage of the transistor T25, thus, depends upon the voltage drop VI2 developed across the constant current circuit C2 and the base-emitter voltage VF5 developed across the transistor T25. Specifically, the upper limit of the output voltage of the transistor is limited to below Vcc−VI2−VF5. If VF5=0.7 V and VI2=0.6 V, then a maximum output voltage will be 5 V−0.6 V−0.7 V=3.7 V.

The pnp transistor T26 is turned on, causing the base current to flow into the bias circuit 93. If the base-emitter voltage VF6 of the transistor T26 is 0.7 V, then a lower limit of the output voltage of the transistor T26 is restricted to VF6=0.7 V where a voltage drop of the bias circuit 93 is assumed to be zero (0).

Therefore, the voltage of output from each of the operational amplifiers 85*a* and 86*a* falls within a range of 0.7 to 3.7 V which is narrower than a source voltage-to-ground potential range of 0 to 5 V.

Additionally, when an air-fuel ratio of 25 is measured in a lean. burn range of the engine, the sensor current flowing through the A/F sensor 81 shows 22 mA. In this case, the base-emitter voltage VF6 of the pnp transistor T26 increases up to 1.2 V. The output voltage range of each of the operational amplifiers 85*a* and 86*a* will, thus, be decreased to 1.2 to 3.7 V. Note that if VF6=0.7 V as described above, then the sensor current=1 mA in a rich burn range of the engine.

SUMMARY OF THE INVENTION

It is therefore a principal object of the present invention to avoid the disadvantages of the prior art.

It is another object of the present invention to increase an input/output voltage range of an operational amplifier used in a gas concentration measuring device for improving the accuracy in measuring the concentration of gas.

According to one aspect of the invention, there is provided a gas concentration measuring apparatus which comprises a gas concentration sensor exposed to a gas and a voltage applying circuit. The gas concentration sensor is responsive to application of voltage to produce a current signal indicative of concentration of the gas. The voltage applying circuit includes an operational amplifier which operates on a source voltage developed between a first and a second source terminal thereof connected to a voltage source. The operational amplifier outputs voltage for developing the voltage applied to the gas concentration sensor which has a level changing as a function of voltage inputted to the operational amplifier. The operational amplifier is designed to have an amplitude of each of the voltages inputted to and outputted from the operational amplifier which falls within a given input/output voltage range defined between an upper limit and a lower limit of a source voltage range of the voltage developed by the voltage source between the first and second source terminals of the operational amplifier and near at least one of the upper and lower limits of the source voltage range.

In the preferred mode of the invention, a difference between an upper limit of the input/output voltage range and the upper limit of the source voltage range is less than or equal to 0.6 V.

A difference between a lower limit of the input/output voltage range and the lower limit of the source voltage range may also be less than or equal to 0.6 V.

The gas concentration sensor measures the concentration of a preselected component of exhaust gasses of an engine mounted in an automotive vehicle. The first source terminal of the operational amplifier is connected to a positive terminal of a single battery installed in the vehicle, while the second source terminal is kept at a reference potential.

The voltage source may alternatively be a constant voltage source for a digital signal connecting with the first source terminal of the operational amplifier. The upper limit of the input/output voltage range lies between the voltage provided by the constant voltage source and the voltage provided by the constant voltage source minus 0.6 V, while the lower limit of the input/output voltage range lies between a ground potential and the ground potential plus 0.6 V.

The operational amplifier has an npn transistor disposed in an output stage thereof. The npn transistor serves as a current sink element and connects at an emitter with ground and at a collector with an output terminal of the operational amplifier.

The operational amplifier also has a pnp transistor disposed in the output stage thereof. The pnp transistor serves as a current source element and connects at an emitter with the voltage source and at a collector with an output terminal of the operational amplifier.

The operational amplifier includes a first input stage to which a higher voltage is inputted and a second input stage to which a lower voltage is inputted.

The operational amplifier is designed to have a rail-to-rail structure.

A resistor circuit, a voltage signal outputting circuit, and a resistor changing circuit are further provided. The resistor circuit is disposed between the output terminal of the operational amplifier and the gas concentration sensor. The voltage signal outputting circuit outputs voltage appearing across the resistor circuit changing as a function of the current signal flowing through the gas concentration sensor. The resistor changing circuit changes a resistor value of the resistor circuit as a function of a value of the current signal.

The resistor changing circuit decreases the resistor value of the resistor circuit as the concentration of the gas increases.

According to another aspect of the invention, there is provided a gas concentration measuring apparatus which comprises a gas concentration sensor exposed to a gas and a first and a second operational amplifier. The gas concentration sensor produces a current signal indicative of concentration of the gas when input voltage is developed across a first and a second terminal of the gas concentration sensor. The first operational amplifier operates on a source voltage developed between a first and a second source terminal thereof connected to a voltage source and outputs voltage to develop a first electric potential at the first terminal of the gas concentration sensor. The voltage outputted from the first operational amplifier changes as a function of voltage inputted to the first operational amplifier. The second operational amplifier operates on the source voltage developed between a first and a second source terminal thereof connected to the voltage source and outputs voltage to develop a second electric potential at the second terminal of the gas concentration sensor for creating the input voltage applied to the gas concentration sensor. The voltage outputted from the second operational amplifier changes as a function of voltage inputted to the second operational amplifier. Each of the first and second operational amplifiers is designed to have an amplitude of each of the voltages inputted thereto and outputted therefrom which falls within a given input/output voltage range defined between an upper limit and a lower limit of a source voltage range of the voltage developed by the voltage source between the first and second source terminals of one of the first and second operational amplifiers and near at least one of the upper and lower limits of the source voltage range.

In the preferred mode of the invention, a resistor circuit and a voltage signal outputting circuit are further provided. The resistor circuit is disposed between an output terminal of the first operational amplifier and the gas concentration sensor. The voltage signal outputting circuit outputs voltage appearing across the resistor circuit changing as a function of the current signal flowing through the gas concentration sensor.

A resistor changing circuit is further provided which changes a resistor value of the resistor circuit as a function of a value of the current signal.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 8 is a circuit diagram which shows an internal structure of each of operational amplifiers 14a and 16a;

DESCRIPTION OF THE PREFERRED EMBODIMENTS

Figure 3:
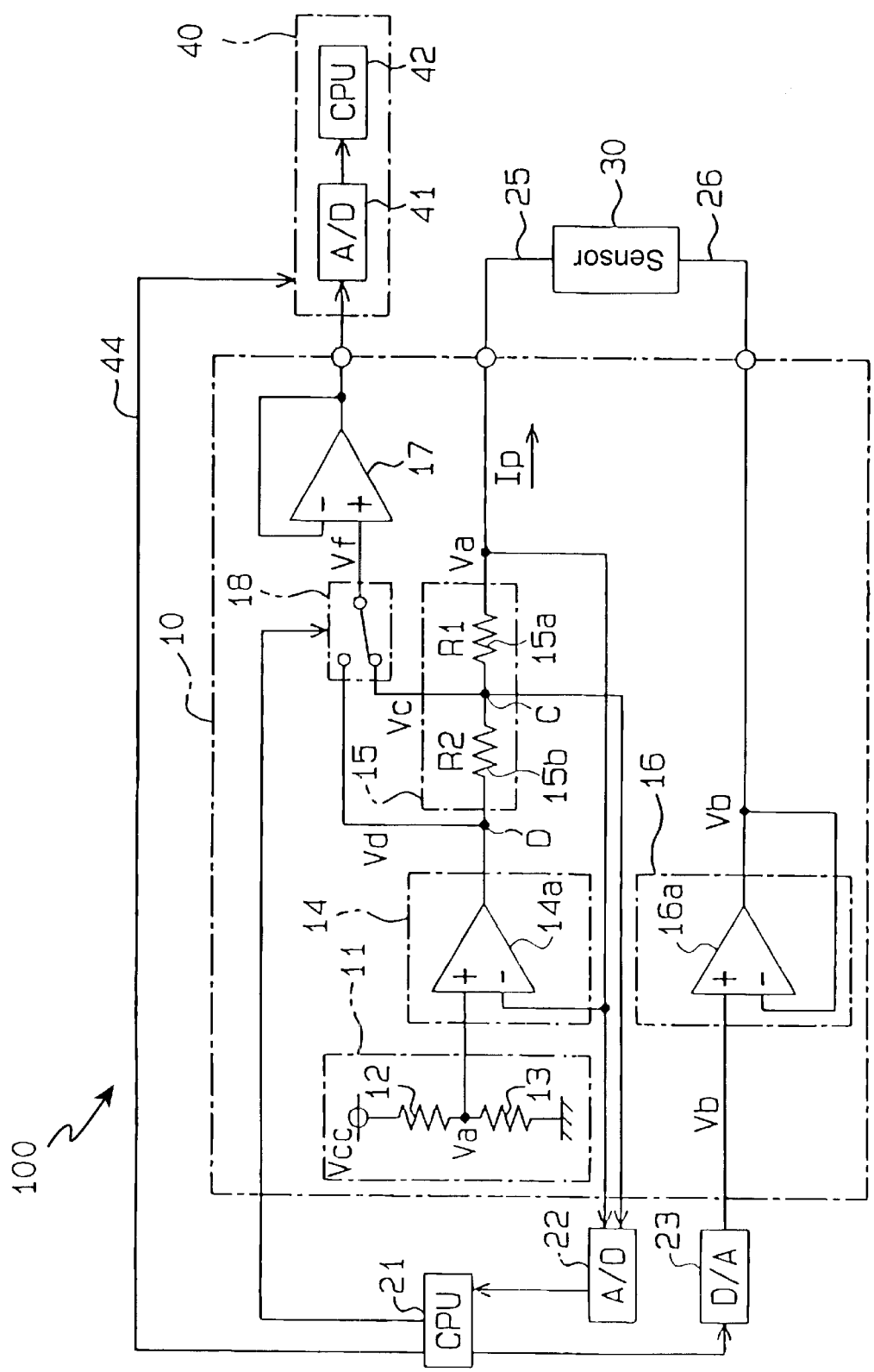
FIG. 3 is a circuit diagram which shows an air-fuel ratio measuring device according to the first embodiment of the invention.

Referring now to the drawings, wherein like numbers refer to like parts in several views, particularly to FIG. 3, there is shown an air-fuel ratio measuring device 100 according to the present invention which is used in air-fuel ratio feedback (F/B) control for gasoline-injection engines of automotive vehicles. The air-fuel ratio measuring device 100 is designed to measure a gaseous content of emissions from the engine to determine the air-fuel (A/F) ratio of mixture sucked into the engine.

The air-fuel ratio measuring device 100 includes an air-fuel ratio measuring circuit 10 and an air-fuel (A/F) sensor 30. The air-fuel ratio measuring circuit 10 is connected to an electric control unit (ECU) 40. The ECU 40 performs the air-fuel ratio F/B control in two control modes: a stoichiometric air-fuel ratio control mode and a lean burn control mode selectively based on engine operating conditions. In the stoichiometric air-fuel ratio control mode, the air-fuel ratio is adjusted to a target value that is a stoichiometric air-fuel ratio of 14.7. In the lean burn control mode, the air-fuel ratio is adjusted to a target value that is a given air-fuel ratio of, for example, 22 within a lean burn range.

The A/F sensor 30 is installed in an exhaust pipe of the engine and designed to produce a limiting current when applied with the voltage. The limiting current is picked up in the form of voltage through a current-detecting resistor and converted into a digital signal through an A/D converter operating within a given input voltage range (0–5 V) which is, in turn, outputted to the ECU 40. The air-fuel ratio measuring device 100 is, as will be explained in detail later, designed to change the resistance value of the current-detecting resistor selectively when the air-fuel ratio lies within a stoichiometric air-fuel ratio range and when it lies within another air-fuel ratio range in order to achieve detection of the air-fuel ratio with high accuracy over a wide range.

Figure 4:
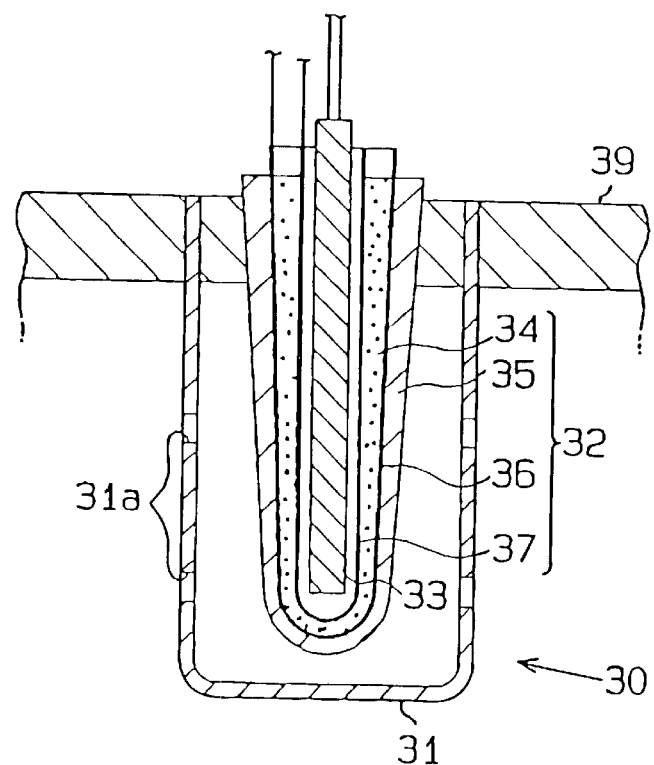
FIG. 4 is a vertical cross sectional view which shows an internal structure of an air-fuel ratio sensor.

The A/F sensor 30 is, as clearly shown in FIG. 4, installed in an exhaust pipe 39 of the engine and exposed to the exhaust gas. The A/F sensor 30 includes generally a cup-shaped cover 31, a sensing body 32, and a heater 33. The cover 31 has formed in a side wall a plurality of holes 31a through which the exhaust gas passes. The sensing body 32 is designed to produce a limiting current as a function of oxygen concentration in a lean air-fuel ratio range and concentrations of unburnt gasses such as CO, HC, and $H_2$ in a rich air-fuel ratio range.

The sensing body 32 consists of a solid electrolyte layer 34, a diffusion resistive layer 35, an exhaust gas-side electrode layer 36, and an atmosphere-side electrode layer 37. The exhaust gas-side electrode layer 36 is formed over an outer surface of the solid electrolyte layer 34. The atmosphere-side electrode layer 37 is formed over an inner surface of the solid electrolyte layer 34. The diffusion resistive layer 35 is formed over the exhaust gas-side electrode layer 36 with plasma spraying. The solid electrolyte layer 34 is made of an oxygen ion conductive sintered oxide body in which CaO, MgO, $Y_2O_3$, and $Yb_2O_3$ are solved as fixing agents in $ZrO_2$, $HfO_2$, $ThO_2$, and $Bi_2O_3$. The diffusion resistive layer 35 is made of a heat-resisting inorganic matter such as alumina, magnesia, silica, spinel, and mullite. The exhaust-side electrode layer 36 and the atmosphere-side electrode layer 37 are both made of a noble metal with a high catalytic activity such as platinum and have surfaces plated chemically with a porous material.

The heater 33 is disposed within a chamber formed inside the atmosphere-side electrode layer 37 and heats the whole of the sensing body 32. The heater 33 has a heat-producing capacity sufficient to activate the sensing body 32.

The sensing body 32 produces a limiting current as a function of the concentration of oxygen in a zone leaner than the stoichiometric air-fuel ratio. The value of the limiting current depends upon the area of the exhaust gas-side electrode layer 36, and the thickness, porosity, and average pore diameter of the diffusion resistive layer 35. The sensing body 32 is designed to measure the concentration of oxygen linearly and requires keeping sensor elements thereof above a high temperature as much as 600° C. for activation of the sensing body 32. To this end, the heater 33 is provided to heat the sensing body 32 up to an activating temperature range. In a zone richer than the stoichiometric air-fuel ratio, the concentration of unburnt gases such as carbon monoxide (CO) etc. changes lineary with a change in air-fuel ratio, and the sensing body 32 produces a limiting current as a function of the concentration of CO etc.

Figure 5:
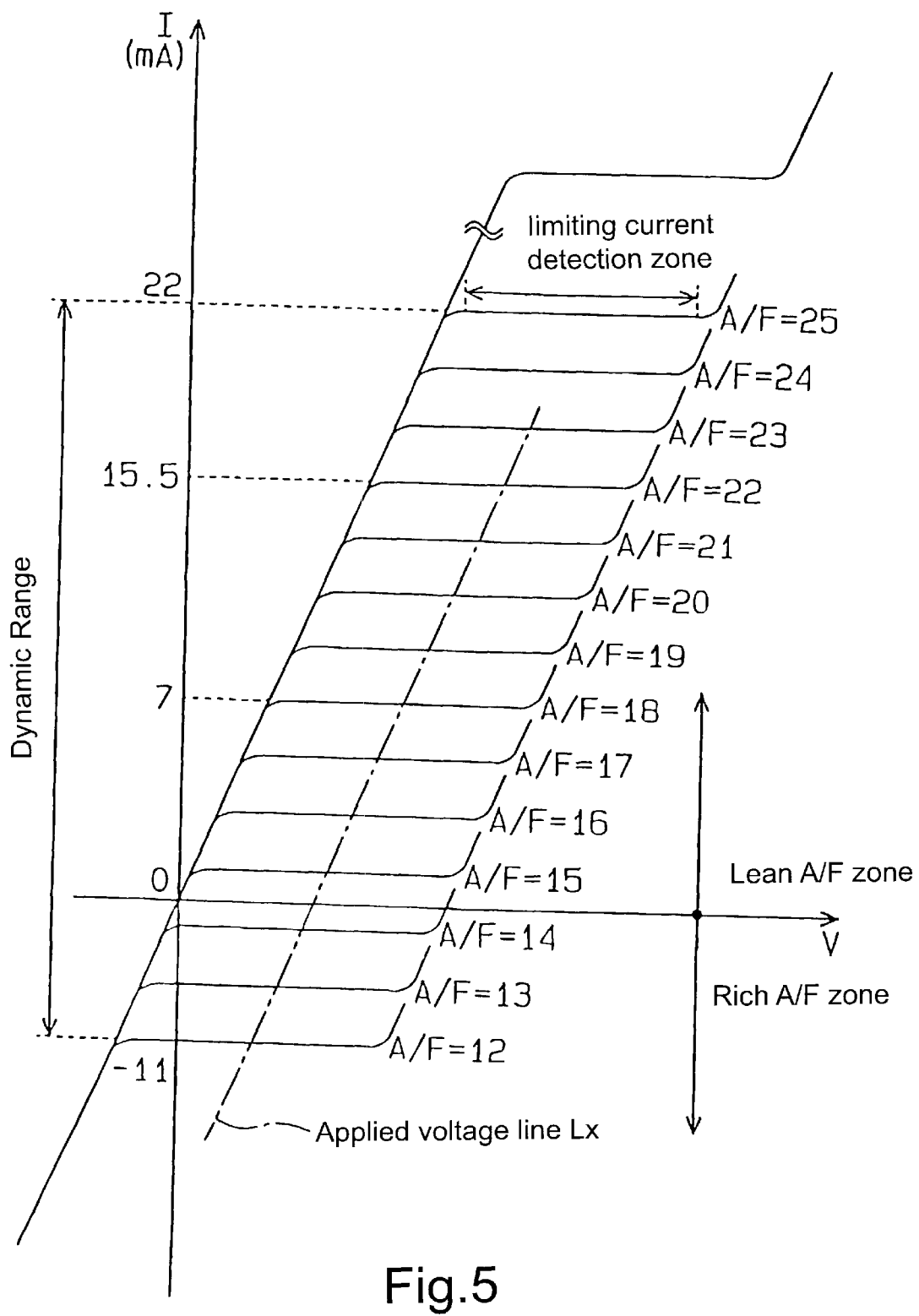
FIG. 5 is a graph which shows voltage-current (V-I) characteristics of the sensor in FIG. 4.

FIG. 5 shows voltage-current (V-I) characteristics of the sensing body 32.

As will be apparent from the drawing, the current flowing through the solid electrolyte layer 34 of the sensing body 32 which is proportional to the air-fuel ratio and the voltage applied to the solid electrolyte layer 34 have linear characteristics. Each straight line segment extending parallel to the abscissa axis represents a limiting current detection zone in which the A/F ratio can be specified by the limiting current detected through the sensor body 32. A change in limiting current corresponds to a change in A/F (i.e., the degree of richness or leanness of mixture). Specifically, the more the A/F ratio is shifted to the lean side, the more the limiting current increases, while the more the A/F ratio is shifted to the rich side, the more the limiting current decreases.

A zone lower in voltage than each of the limiting current detection zones through which a linear line passes is a resistance dominated zone. The inclination of the linear line depends upon an internal resistance of the solid electrolyte layer 34 of the sensing body 32. The internal resistance usually changes with a change in temperature of the solid electrolyte layer 34. Specifically, a decrease in temperature of the sensing body 32 causes the internal resistance of the solid electrolyte layer 34 to be increased, thus decreasing the inclination of the linear line. In the case shown, a dynamic range extends from an air-fuel ratio of 12 to an air-fuel ratio of 25.

Referring back to FIG. 3, the air-fuel ratio measuring circuit 10 is designed to control the voltage applied to the A/F sensor 30 and monitor the current Ip flowing through the A/F sensor 30. The air fuel ratio measuring circuit 10 includes a reference voltage circuit 11, amplifying circuits 14 and 16, a sensor current detecting circuit 15, and a switching circuit 18.

The reference voltage circuit 11 consists of voltage-dividing resistors 12 and 13 and produces a fraction of constant voltage Vcc as a reference voltage Va (=2.5 V, for example).

The amplifying circuit 14 includes an operational amplifier 14a which connects at a non-inverting input (+) with a junction of the resistors 12 and 13 of the reference voltage circuit 11 and at an output with a terminal 25 of the A/F sensor 30 through the sensor current detecting circuit 15. The terminal 25 of the A/F sensor 30 leads to the atmosphere-side electrode layer 37 and is applied with the voltage Va (=2.5 V) identical with the reference voltage Va. The terminal 25 also connects with an inverting input (−) of the operational amplifier 14a so that the voltage Va appearing at the terminal 25 is inputted to an A/D converter 22.

Figure 8:
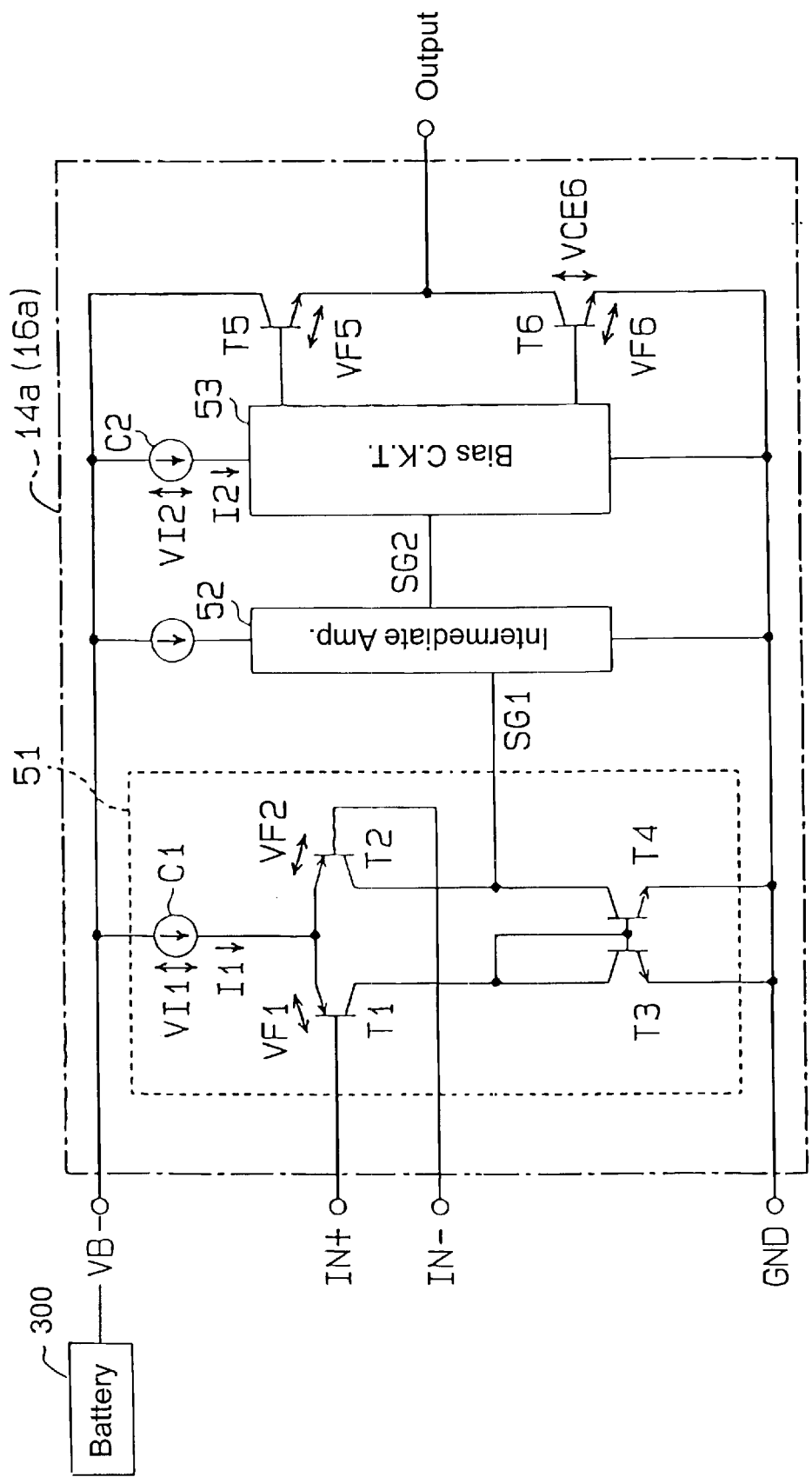

The operational amplifier 14a is disposed electrically between the battery voltage VB (=12 V) of a battery 300 installed in the vehicle and the ground (GND) potential (see FIG. 8). Specifically, the operational amplifier 14a is signed to perform the so-called rail-to-rail operation and has a voltage output range near an upper and/or a lower limit of an output range of the voltage source (i.e., the battery). In practice, an output of the operational amplifier 14a is restricted to within a range from a maximum voltage (5 V) readable by the ECU 40 and a minimum voltage (0.38 V) in the rail-to-rail operation, which will be discussed later in detail.

The sensor current detecting circuit 15 consists of a pair of resistors 15a and 15b connected series between the output of the operational amplifier 14 and the terminal 25 of the A/F sensor 30 and detects the sensor current Ip as indicating the A/F ratio. The voltage Vc appearing a junction, as indicated by C in the drawing, of the resistors 15a and 15b is inputted to the A/D converter 22.

The voltage developed across the resistor 15a of the sensor current detecting circuit 15 is inputted to a bias-controlling CPU 21 through the A/D converter 22 in the form of a digital signal. The CPU 21 measures the sensor current (i.e., the limiting current) Ip. based on the voltage of the digital signal from the A/D converter 22 and determines the voltage to be applied to the A/F sensor 30. In practice, the CPU 21 determines the voltage to be applied to the A/F sensor 30 along the applied voltage line Lx in FIG. 5 based on the measured sensor current. Ip and converts it into a command voltage Vb through the D/A converter 23 which is, turn, inputted to the operational amplifier 16a of the amplifying circuit 16.

The operational amplifier 16a connects at a non-inverting input (+) with the D/A converter 23 and at an inverting input (−) with an output thereof. The output is connected to the terminal 26 of the A/F sensor 30. The terminal 26 leads to the exhaust gas-side electrode layer 36 of the A/F sensor 30 is applied with the controlled voltage Vb identical with the command voltage Vb inputted to the operational amplifier 16a. The operational amplifier 16a, like the operational amplifier 14a, is designed to perform the rail-to-rail operation.

Therefore, the air-fuel ratio measuring circuit 10 applies the reference voltage Va and the controlled voltage Vb to the terminals 25 and 26 of the A/F sensor 30, respectively. When the controlled voltage Vb is lower than the reference voltage Va (Vb<Va), it will cause the A/F sensor 30 to undergo the positive bias. Alternatively, when the controlled voltage Vb is higher than the reference voltage Va (Vb>Va), it will cause the A/F sensor 30 to undergo the negative bias. In either case, the sensor current Ip resulting from the application of the voltage to the A/F sensor 30 is measured by the CPU 21 through the A/D converter 22 as a potential difference developed across the resistor 15a (i.e., Vc−Va).

The air-fuel ratio measuring circuit 10 also includes a voltage follower 17 which receives the sensor current Ip flowing through the sensor current detecting circuit 15 in the form of a voltage signal and outputs it to the ECU 40. The voltage follower 17 connects at a non-inverting input (+) with the junction C of the resistors 15a and 15b or the junction D of the resistor 15b and the operational amplifier 14a selectively through the switch circuit 18. Specifically, when the switch circuit 18 establishes, as shown in the drawing, communication between the voltage follower 17 and the junction C, the voltage Vc is inputted to the voltage follower 17 as an input voltage Vf. Therefore, a voltage drop (i.e., a difference between the voltages Vc and Va) developed across only the resistor 15b by the flow of the sensor current Ip through the resistors 15a and 15b is monitored by the ECU 40 to determine the A/F ratio. Alternatively, when the switch circuit 18 establishes communication between the voltage follower 17 and the junction D, the voltage Vd is inputted to the voltage follower 17 as the input voltage Vf. Therefore, a voltage drop (i.e., a difference between the voltages Vd and Va) developed across the resistors 15a and 15b by the flow of the sensor current Ip is monitored by the ECU 40 to determine the A/F ratio. This switching operation is controlled by CPU 21, and information thereon is inputted to the ECU 40 through a signal line 44.

The voltage output from the voltage follower 17 is inputted to the CPU 42 through the A/D converter 41 of the ECU 40. The CPU 42 determines a difference between the voltage (i.e., an A/F ratio value derived as a function of the sensor current Ip) inputted through the A/D converter 41 and the reference voltage Va provided in the air-fuel ratio measuring circuit 10 to calculate an actual air-fuel (A/F) ratio. In this embodiment, the source voltage of the A/D converter 41 is 5 V, and an input voltage range of the A/D converter 41 is 0 to 5 V. Thus, if the A/D converter 41 has an 8-bit structure, the CPU 42 expresses an actual value of the A/F ratio in one of 256 divisions of the input voltage range of 0 to 5 V within a dynamic range as shown in FIG. 5.

The air-fuel ratio F/B control performed in the ECU 40 is not the gist of the invention and well known in the art. In brief, the ECU 40 monitors the A/F ratio measured by the air-fuel ratio measuring circuit 10 and feedback-controls the quantity of fuel supplied from each injector to one of cylinders of the engine to have an actual air-fuel ratio reach a target one according to a control algorithm used in the so-called modern control or the PID control. When the engine is in low load conditions, the ECU 40 performs lean burn control. Alternatively, when the engine is in intermediate or high load conditions, the ECU 40 performs standard stoichiometric air-fuel ratio control.

The operation of the switching circuit 18 will be described below in terms of two methods of measuring the A/F ratio in a near stoichiometric A/F ratio zone ranging from an A/F ratio of 12.8 to 18 in which the stoichimetoric A/F ratio control is performed and out-of-stoichiometric A/F ratio zones ranging from an A/F ratio of 12 to 12.8 and from 18 to 25 in which the lean burn control is performed. Here, it is assumed that the reference voltage Va is 2.5 V, the sensor current Ip when the A/F ratio=18 is 7 mA, and the sensor current Ip when the A/F ratio=25 is 22 mA. It is also assumed that resistance values R1 and R2 of the resistors 15a and 15b of the sensor current detecting circuit 15 are 113Ω and 244Ω, respectively. In the near stoichiometic A/F ratio zone (A/F ratio=12.8–18), when the voltages Vc and Vd appearing at the junctions C and D in FIG. 3 show maximum values as listed below, the A/F ratio will be 18.

Vc=3.291 V

Vd=4.999 V

The voltage Vc is calculated by adding the reference voltage Va to the product of the sensor current Ip and the resistance value R1 of the resistor 15a (Vc=Ip·R1+Va). The voltage Vd is calculated by adding the reference voltage Va to the product of the sensor current Ip and the resistance values R1 and R2 of the resistors 15a and 15b (Vd=Ip·(R1+ R2)+Va).

The voltages Vc and Vd are both within the voltage range of 0 to 5 V handled by the A/D converter 41 of the ECU 40 so that they can be processed by the A/D converter 41 correctly. It is, as already mentioned, advisable that as great a voltage change per unit change in A/F ratio as possible be established for improving the accuracy in detecting the A/F ratio.

A change in voltage Vc per unit change in A/F ratio in case where the stoichiometric air-fuel ratio of 14.7 is used as a reference value is (3.291 V−2.5 V)/(18−14.7)=0.239 V Similarly, a change in voltage Vd per unit change in A/F ratio is (4.999 V−2.5 V)/(18−14.7)=0.757 V It is, thus, appreciated that the use of the voltage Vd as the input voltage Vf to the voltage follower 17 enables the A/F ratio to be measured with higher accuracy as compared with use of the voltage Vc.

Figure 6:
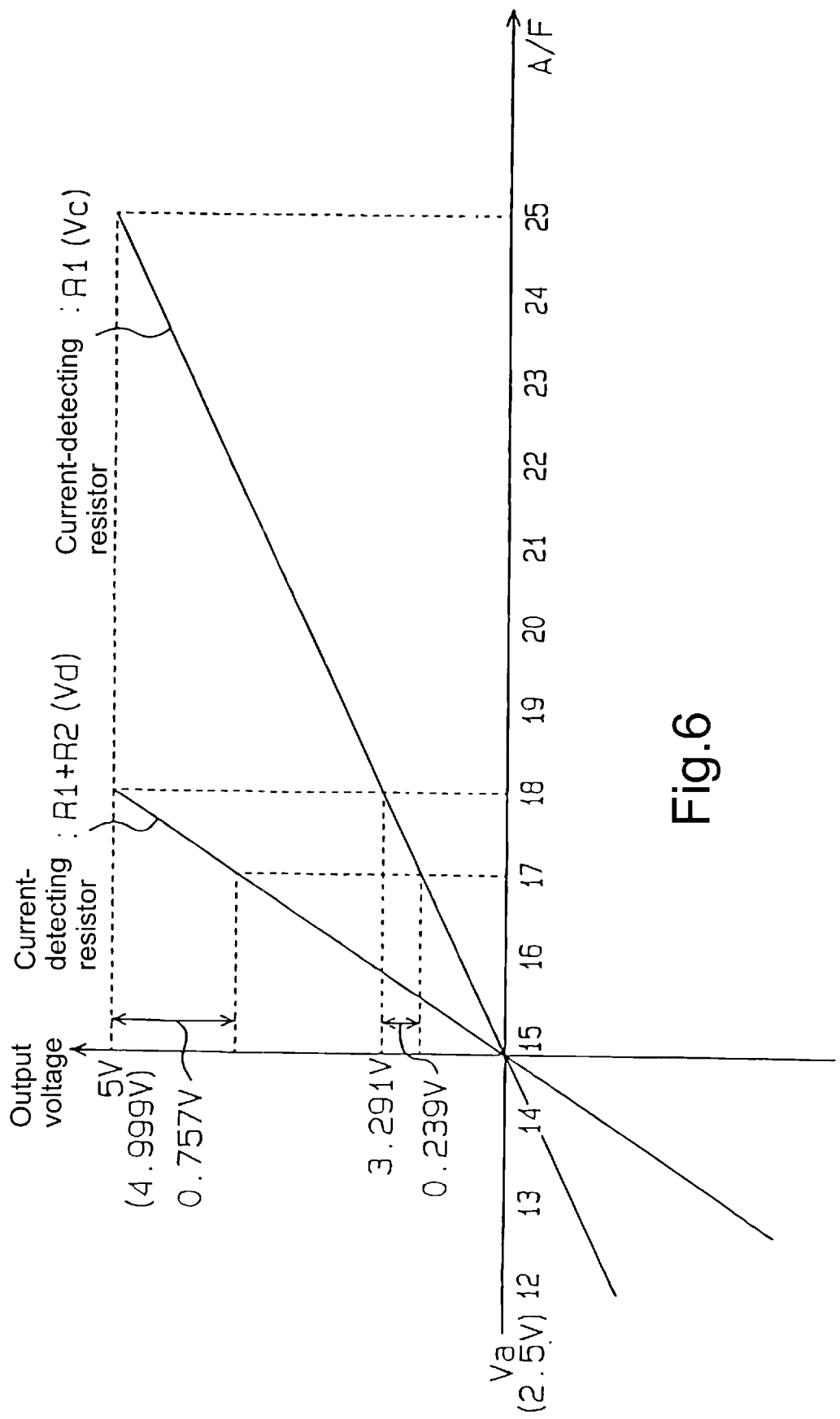
FIG. 6 is a graph which shows the relation between the voltage outputted to the voltage follower 17 through the switching circuit 18 and the A/F ratio measured by the A/F sensor 30.

The relation between the voltage outputted to the voltage follower 17 through the switching circuit 18 and the A/F ratio measured by the A/F sensor 30 is shown FIG. 6 in terms of two cases where the voltage Vc is outputted using only the resistor 15a (R1) and where the voltage Vd is outputted using the resistors 15a and 15b (R1+R2). The comparison between voltage changes between A/F ratios of 17 and 18 shows that the use of the voltage Vd as the input voltage Vf to the voltage follower 17 increases the accuracy in mesuring the A/F ratio.

In the out-of-stoichiometric air-fuel zones (A/F ratio= 12–12.8, 18–25), when the voltages Vc and Vd appearing at the junctions C and D in FIG. 3 show maximum values as listed below, the A/F ratio will be 25 (Ip=22 mA).

Vc=4.986 V

Vd=10.354 V

Since the voltage range handled by the A/D converter 41 of the ECU 40 is, as described above, 0 to 5 V, the A/D converter 41 can handle the voltage Vc, but not the voltage Vd. The voltage Vc is, thus, used as the input voltage Vf to the voltage follower 17. Specifically, a maximum air-fuel ratio of 25 is, as shown in FIG. 6, measured by use of only the resistor 15a (R1) in the out-of-stoichiometric air-fuel ratio zones.

Figure 7:
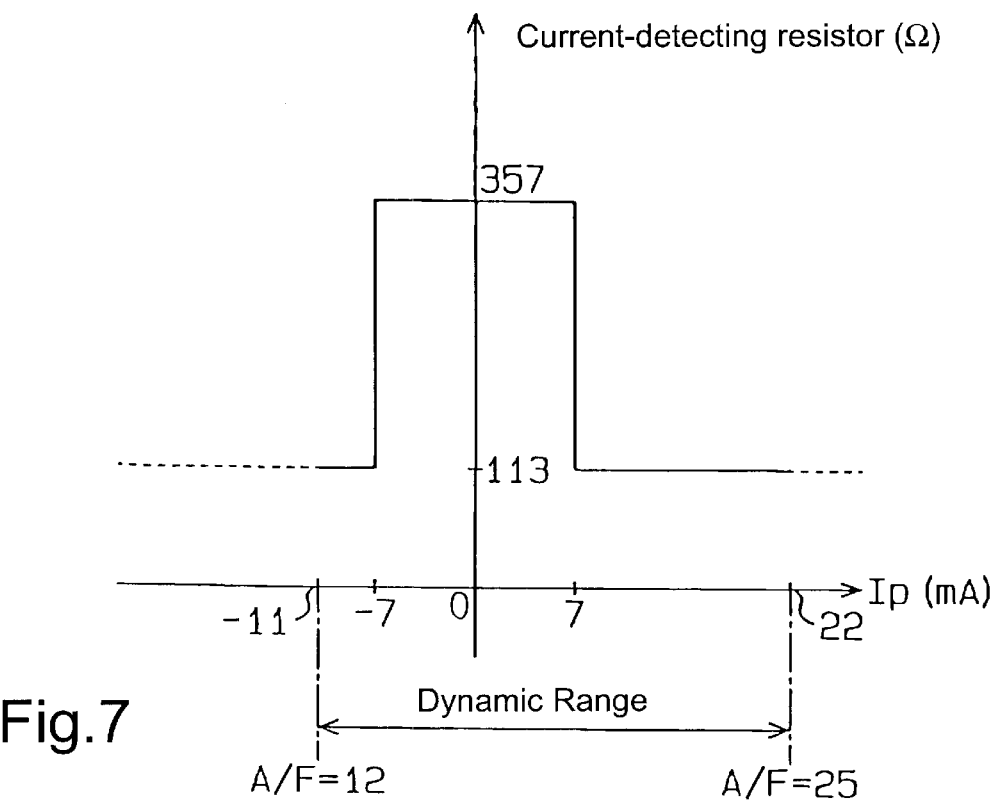
FIG. 7 is a graph which shows a preferred relation between the sensor current Ip(mA) and a resistance value ($\Omega$) of the sensor current detecting circuit 15.

FIG. 7 shows a preferred relation between the sensor current Ip(mA) and a resistance value (Ω) of the sensor current detecting circuit 15.

For instance, when the A/F ratio=12, Ip=−11 mA. When the A/F ratio=12.8, Ip=−7 mA. When the A/F ratio=18, Ip=7 mA. When the A/F ratio=25, Ip=22 mA. The graph shows that it is advisable that the sum of the resistance values R1 and R2 be selected to show 357Ω when −7 mA≦Ip≦7 mA (i.e., the near stoichiometric air-fuel ratio zone) and that the resistance value R1 be selected to have 113Ω when −10 mA≦Ip≦7 mA and 7 mA≦Ip≦22 mA (i.e., the out-of-stoichiometric air-fuel ratio zones).

FIG. 8 shows an equivalent circuit of each of the operational amplifiers 14a and 16a designed to perform the rail-to-rail function. The operational amplifiers 14a and 16a have the same circuit structure, and explanation below will refer only to the operational amplifier 14a for the simplicity of explanation. In FIG. 8, circuit components common to typical operational amplifiers are simplified. The operational amplifier 14a connects at a positive terminal VB with the battery 300 installed in the vehicle and operates only on a battery voltage of 12 V. The operational amplifier 14a includes an input circuit 51, an intermediate amplifying circuit 52, and a bias circuit 53.

The input circuit 51 consists of a pair of pnp transistors T1 and T2, a constant current circuit C1 connecting with emitters of the pnp transistors T1 and T2, and a pair of npn transistors T3 and T4 connecting with collectors of the pnp transistors T1 and T2. Input signals IN+ and IN− are inputted to bases of the pnp transistors T1 and T2, respectively. The structure of the input circuit 51 is identical with that of a typical operational amplifier such as the one shown in FIG. 2.

The pnp transistors T1 and T2 operate on the constant current I1 from the constant current circuit C1 and changes the collector currents thereof as a function of a voltage difference between the input signals IN+ and IN−. The npn transistors T3 and T4 operates on the collector currents from the pnp transistors T1 and T2.

Specifically, when the input signal IN+ is higher in voltage than the input signal IN−, it will cause the collector current of the pnp transistor T2 to increase, so that the collector voltage of the npn transistor T4 is elevated. Alternatively, when the input signal IN+ is lower in voltage than the input signal IN−, it will cause the collector current of the pnp transistor T1 to increase, so that the base current flows in the npn transistors T3 and T4, thereby turning on the npn transistors T3 and T4 so that the collector voltage of the transistor T4 drops.

The collector voltage of the npn transistor T4 is outputted as a signal SG1 to the intermediate amplifying circuit 52. The signal SG1 is amplified and outputted as a signal SG2 to the bias circuit 53. The bias circuit 53 operates on the constant current I2 from the constant current circuit C2 and activates the npn transistor T5 working as a current source or the npn transistor T6 working as a current sink.

When the input signal IN+ is higher in voltage than the input signal IN−, the bias circuit 53 activates the npn transistor T5 to elevate an output voltage. Alternatively, when the input signal IN+ is lower in voltage than the input signal IN−, the bias circuit 53 activates the npn transistor T6 to decrease the output voltage. In order to have a positive or a negative current flow through the A/F sensor 30 as a function of air-fuel ratio of emissions from the engine, it is necessary for the output of the operational amplifier 14a to be sourced by the sensor current Ip or sink the sensor current Ip.

The operational amplifier 14a will also be discussed below in terms of (1) restriction on input voltage, (2) restriction on a maximum output voltage, and (3) restriction on a minimum output voltage.

Restriction on Input Voltage

The pnp transistors T1 and T2 operate on the constant current I1 from the constant current circuit C1 applied with the battery voltage VB and allow the base current to flow. The voltage of the input signal IN+, thus, depends upon the voltage drop VI1 developed across the constant current circuit C1 and the base-emitter voltage VF1 developed across the transistor T1, so that the transistors T1 and T2 operate normally within a voltage range below VB−VI1−VF1. Similarly, the voltage of the input signal IN− depends upon the voltage drop VI1 and the base-emitter voltage VF2 developed across the transistor T2, so that the transistors T1 and T2 operate normally within a voltage range below VB−VI1−VF2. For instance, if VI1=0.6 V and VF1=VF2=0.7 V, then a maximum voltage of each of the input signals IN+ and IN− is restricted to 12 V−0.6 V−0.7 V=10.7 V. The input circuit 51 includes the pnp transistors T1 and T2 and thus operates normally on a voltage lower than the ground potential. Therefore, when the voltage of each of the input signals IN+ and IN− lies within a range of 0 V to 10.7 V, the input circuit 51 operates to receive the input signals IN+ and IN− normally.

Restriction on Maximum Output Voltage

The transistor T5 disposed in an output stage of the operational amplifier 14a is implemented with an npn transistor and operates on the constant current I1 from the constant current circuit C1 applied with the battery voltage VB and allow the base current to flow. The output voltage, thus, depends upon the voltage drop VI2 developed across the constant current circuit C2 and the base-emitter voltage VF5 developed across the transistor T5, so that it is limited to below VB−VI2−VF5. For instance, if VF5=0.7 V and VI2=0.6 V, then a maximum output voltage is restricted to 12 V−0.6 V−0.7 V=10.7 V. The input circuit 51 includes the pnp transistors T1 and T2 and operates normally even when the input voltages are at ground potential. The input circuit 51, thus, works normally when the input signals IN+ and IN− lie within a voltage range of 0 to 10.7 V.

Restriction on Minimum Output Voltage

The transistor T6 is implemented with an npn transistor and operates to allow the base current to flow from the bias circuit 53. The output voltage, thus, does not depend upon the base-emitter voltage VF6 of the transistor T6, but is restricted by the collector-emitter voltage VCE6 of the transistor T6. For instance, if VCE6=0.38 V, then a minimum output voltage is restricted to 0.38 V.

Therefore, the voltage of output from the operational amplifier 14a operating on the battery voltage VB falls within a range of 0.38 to 10.7 V.

The output voltage of the operational amplifier 14a is inputted to the A/D converter 41 through the voltage follower 17. The input voltage range of the A/D converter 41 is, as described above, 0 to 5 V. The input and output voltage ranges (i.e., an operating voltage range) in which the operational amplifier 14a is to be operated are, thus, 0.38 to 5 V which are wider than that of a typical operational amplifier. Specifically, the voltage range in which the A/F ratio is measured is wider than that in a conventional air-fuel ratio measuring device such as the one shown in FIG. 1.

Figure 9:
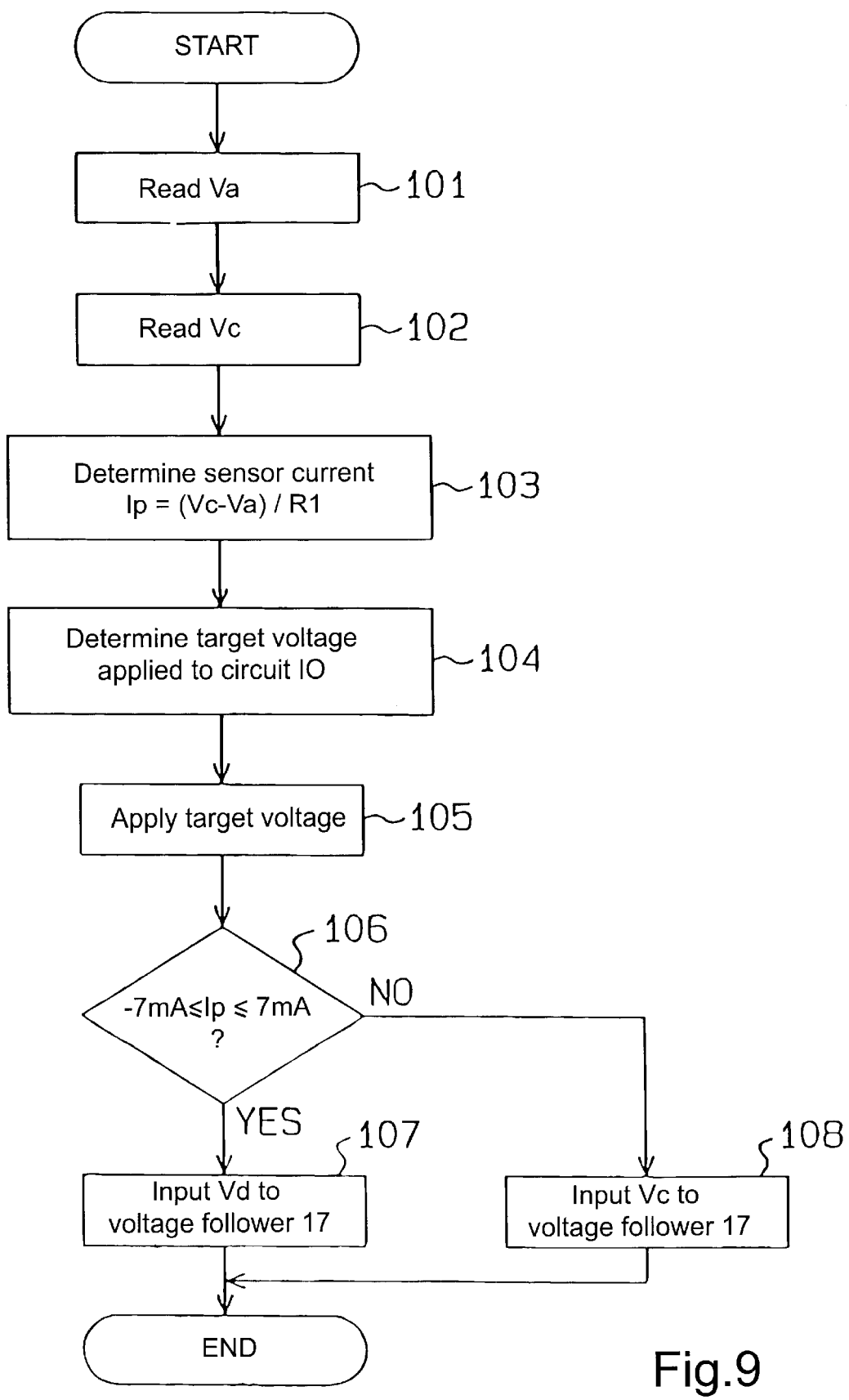
FIG. 9 is a flowchart of a program executed to determine an air-fuel ratio.

FIG. 9 shows a program or logical steps performed by the CPU 21 cyclically at intervals of 4 ms, for example, to determine the A/F ratio.

After entering the program, the routine proceeds to step 101 wherein the CPU 21 monitors the voltage Va appearing at one end of the resistor 15a through the A/D converter 22. The routine proceeds to step 102 wherein wherein the CPU 21 monitors the voltage Vc appearing at the junction of the resistors 15a and 15b through the A/D converter 22. The routine proceeds to step 103 wherein the sensor current Ip is determined using the voltages Va and Vc according to an equation below.

$$Ip=(Vc-Va)/R1$$

where R1 is a resistance value of the resistor 15a.

The routine proceeds to step 104 wherein a target voltage to be applied to the air-fuel ratio measuring circuit 10 is determined by look-up using the map as shown in FIG. 5. Specifically, the voltage corresponding to the sensor current Ip derived in step 103 is looked up using the applied voltage line Lx.

The routine proceeds to step 105 wherein the CPU 21 outputs the command voltage Vb to the operational amplifier 16a of the air-fuel ratio measuring circuit 10 through the D/A converter 23 to apply the target voltage determined in step 104 to the A/F sensor 30.

The routine proceeds to step 106 wherein it is determined whether the sensor current Ip lies within a range of −7 mA to 7 mA (i.e., the near stoichiometric air-fuel ratio zone ranging from an A/F ratio of 12.8 to 18) or not. If a YES answer is obtained meaning that the A/F ratio lies within the near stoichiometric air-fuel ratio zone, then the routine proceeds to step 107 wherein the CPU 21 actuates the switching circuit 18 to establish communication between the junction D and the voltage follower 17, thereby inputting the voltage Vd to the A/D converter 41 of the ECU 40 as the input voltage Vf.

If a NO answer is obtained in step 106 meaning that the A/F ratio lies within either of the out-of-stoichiometric air-fuel ratio zones ranging from an A/F ratio of 12 to 12.8 and from an A/F ratio of 18 to 25, then the routine proceeds to step 108 wherein the CPU 21 actuates the switching circuit 18 to establish communication between the junction C and the voltage follower 17, thereby inputting the voltage Vc to the A/D converter 41 as the input voltage Vf.

The CPU 42 monitors information on a selected position of the switching circuit 18 inputted through the signal line 44 so that the A/F ratio can be determined correctly based on a difference between the input voltage Vf and the reference voltage Va even when the input voltage Vf has a value common to both the near stoichiometric air-fuel ratio zone and one of the out-of-stoichiometric air-fuel ratio zones.

The air-fuel ratio measuring device 100 of this embodiment, as described above, uses the operational amplifier 14a and 16a each designed to have the rail-to-rail structure which has an increased output voltage amplitude near an upper and/or a lower limit of a voltage range (0 to 5 V) of the power supply. The increase in output voltage amplitude of each of the operational amplifiers 14a and 16a will allow the sensor current Ip to be detected within an increased voltage range. In a case where the A/F ratio ranging from 12 to 25 is measured, an output voltage range of each of the operational amplifiers 85a and 86a of the conventional air-fuel ratio measuring device, as shown in FIG. 1, is 0.7 to 3.7 V, and thus, a maximum voltage change per unit change in A/F ratio is approximately 0.23 V ($\approx 3$ V/13), while an output voltage range of each of the operational amplifiers 14a and 16a of this embodiment is 0.38 to 5 V, and a maximum voltage change per unit change in A/F ratio is approximately 0.36 V ($\approx 4.62/13$), thereby resulting in an increase in accuracy in measuring the A/F ratio.

The npn transistor T6 is used in the output stage of each of the operational amplifiers 14a and 16a which has, as already explained, the emitter connected to ground and the collector connected to the output terminal. As compared with the conventional device as shown in FIG. 1, this structure allows the output voltage range of each of the operational amplifiers 14a and 16a to be broadeded. For instance, when the sensor current Ip is 22 mA indicating an A/F ratio of 25, the base-emitter voltage VF6 developed across the pnp transistor T26, as shown in FIG. 2, is elevated up to 1.2 V, however, the output voltage range of each of the operational amplifiers 14a and 16a of this embodiment is allowed to be increased regardless of the base-emitter voltage VF6.

An air-fuel ratio measuring device according to the second embodiment of the invention will be described below with reference to FIGS. 10 and 1.

Figure 1:
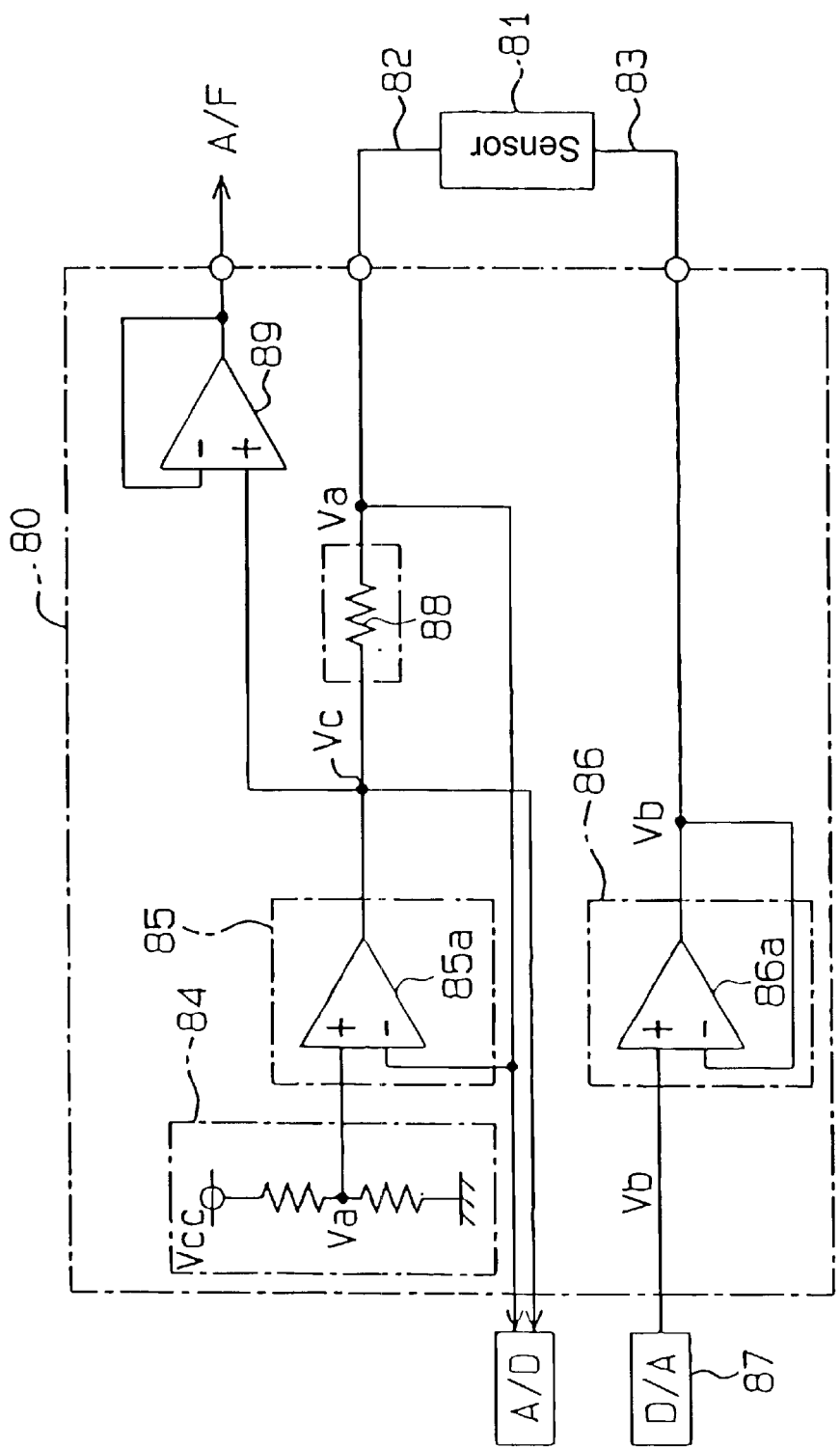
FIG. 1 is a circuit diagram which shows a air-fuel ratio measuring circuit used in a conventional air-fuel ratio measuring device for automotive vehicles.
Figure 2:
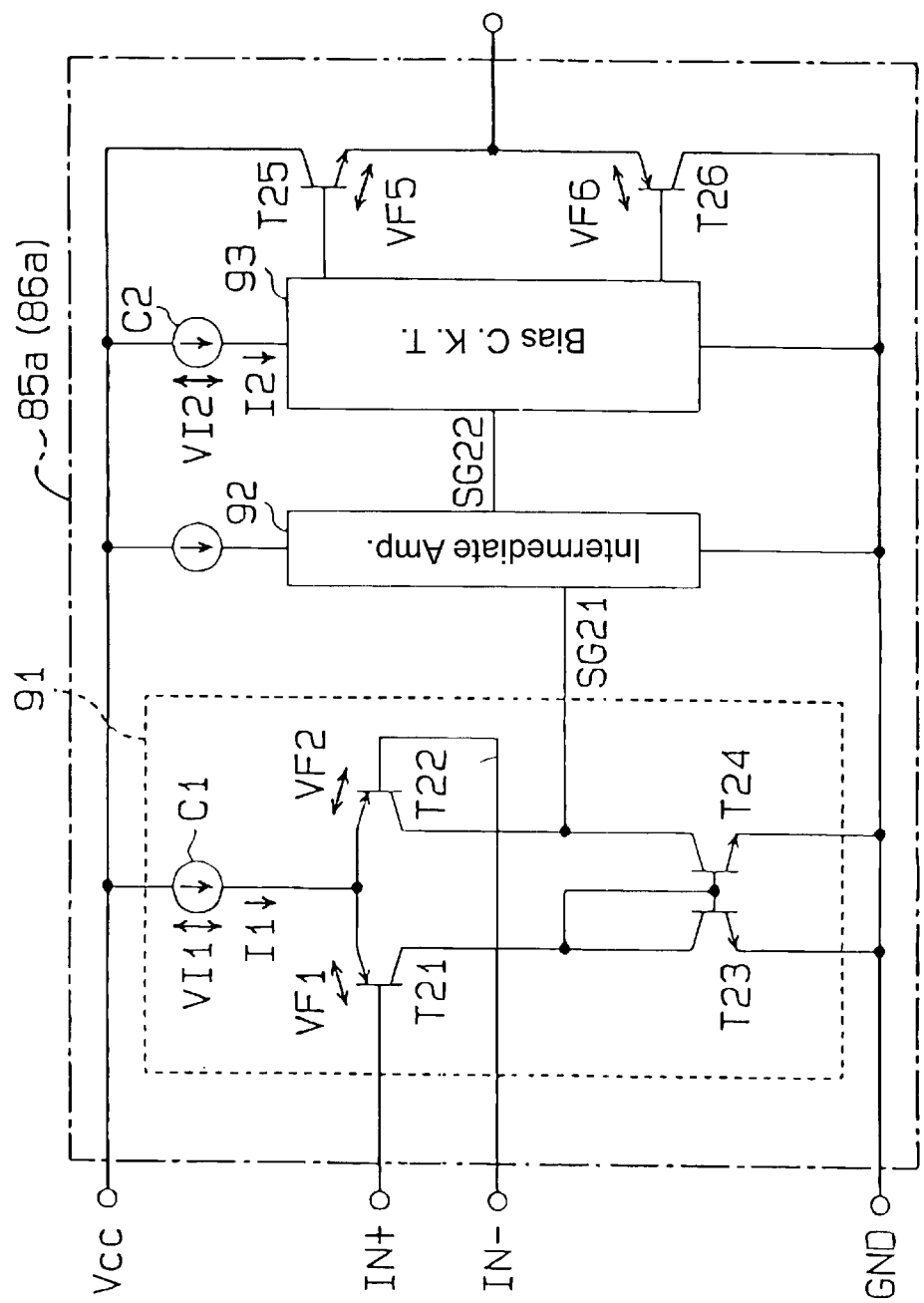
FIG. 2 is a circuit diagram which shows an internal structure of an operational amplifier used in the air-fuel ratio measuring circuit in FIG. 1.

The air-fuel ratio measuring device of this embodiment has the same structure as the one shown in FIG. 1 except the structure of each of the operational amplifiers 85a and 85b.

Figure 10:
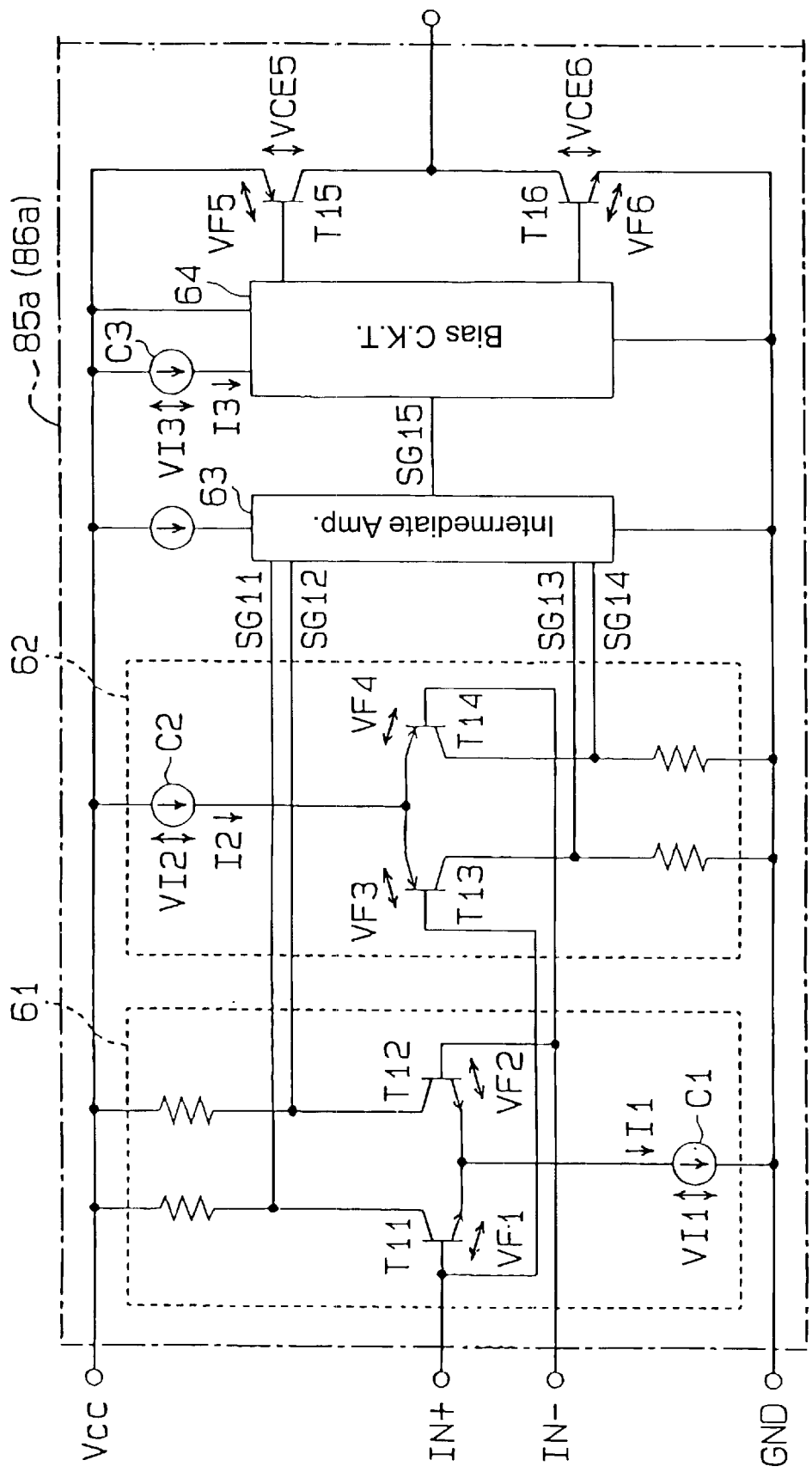
FIG. 10 is a circuit diagram which shows an internal structure of each of operational amplifiers 85a and 86a used in the second embodiment of the invention.

The operational amplifiers 85a and 86a both have a rail-to-rail structure, as shown in FIG. 10, and explanation below will refer only to the operational amplifier 85a for the brevity of disclosures The operational amplifier 85a connects at a positive terminal with a digital signal constant voltage source and is applied with a source voltage Vcc of 5 V. The operational amplifier 85a includes a first input circuit 61, a second input circuit 62, an intermediate amplifying circuit 63, and a bias circuit 64.

The first input circuit 61 consists of a pair of pnp transistors T11 and T12 and a constant current circuit C1 connecting with emitters of the npn transistors T11 and T12. The second input circuit 62 consists of a pair of pnp transistors T13 and T14 and a constant current circuit C2 connecting with emitters of the pnp transistors T13 and T14. Input signals IN+ and IN− are both inputted to the first and second input circuits 61 and 62. The first input circuit 61 is designed to operate normally when the input voltage is high or near the source voltage Vcc, while the second input circuit is designed to operate normally when the input voltage is low or near ground potential (GND).

The npn transistors T11 and T12 of the first input circuit 61 operate on the constant current I1 produced by the constant current circuit C1 and change the collector currents thereof as a function of a voltage difference between the input signals IN+ and IN−. The changes in collector currents of the npn transistors T11 and T12 will cause signals SG11 and SG12 (i.e., collector voltages of the transistors T11 and T12) to be changed.

The pnp transistors T13 and T14 of the second input circuit 62 operate on the constant current I2 produced by the constant current circuit C2 and change the collector currents thereof as a function of a voltage difference between the input signals IN+ and IN−. The changes in collector currents of the pnp transistors T13 and T14 will cause signals SG13 and SG14 (i.e., collector voltages of the transistors T13 and T14) to be changed.

When input voltages, i.e., voltages of the input signals IN+ and IN− are high, near the source voltage Vcc and when the input signals IN+ is higher in voltage than the input signal IN−, it will cause the collector current of the transistor T11 of the first input circuit 61 to be increased, so that the collector voltage of the transistor T12 becomes higher than the collector voltage of the transistor T11 (SG12>SG11). Alternatively, when the input signals IN+ is lower in voltage than the input signal IN−, it will cause the collector current of the transistor T12 to be increased, so that the collector voltage of the transistor T11 becomes higher than the collector voltage of the transistor T12 (SG12<SG11).

When the voltages of the input signals IN+ and IN− are low, near ground potential and when the input signals IN+ is higher in voltage than the input signal IN−, it will cause the collector current of the transistor T14 of the second input circuit 62 to be increased, so that the collector voltage of the transistor T14 becomes higher than the collector voltage of the transistor T13 (SG14>SG13). Alternatively, when the input signals IN+ is lower in voltage than the input signal IN−, it will cause the collector current of the transistor T13 to be increased, so that the collector voltage of the transistor T13 becomes higher than the collector voltage of the transistor T14 (SG14<SG13).

The first input circuit 61, as described above, includes the npn transistors T11 and T12, so that it may operate normally when the input voltages are high. When the input voltages are low, the first input circuit 61 operates normally only above VI1+VF1 or VI1+VF2 under restrictions of the voltage drop VI1 across the constant current C1 and the base-emitter voltages VF1 and VF2 of the transistors T11 and T12.

Conversely, the second input circuit 62 includes the pnp transistors T13 and T14, so that it may operate normally when the input voltages are low. When the input voltages are high, the second input circuit 62 operates normally only below Vcc−VVI2−VF3 or Vcc−VI2−VF4 under restrictions of the voltage drop VI2 across the constant current C2 and the base-emitter voltages VF3 and VF4 of the transistors T13 and T14.

The signals SG11 to SG14 are inputted to the intermediate amplifying circuit 63. When the voltages of the input signals IN+ and IN− near the source voltage Vcc, the intermediate amplifying circuit 63 amplifies a difference between the signals SG11 and SG12 and provides it as a signal SG15 to the bias circuit 64. Conversely, when the voltages of the input signals IN+ and IN− near the ground potential, the intermediate amplifying circuit 63 amplifies a difference between the signals SG13 and SG14 and provides it as the signal SG15 to the bias circuit 64.

The bias circuit 64 operates on the constant current I3 from the constant current circuit C3 and activates the pnp transistor T15 working as a current source or the npn transistor T16 working as a current sink. The pnp transistor T15 is applied at the emitter with the source voltage Vcc and connects at the collector with an output terminal. The npn transistor T16 connects at the emitter with ground and at the collector with the output terminal.

When the input signal IN+ is higher in voltage than the input signal IN−, the bias circuit 64 activates the pnp transistor T15 to elevate the output voltage. The activation of the pnp transistor T15 is accomplished by sinking the base current thereof. Alternatively, when the input signal IN+ is lower in voltage than the input signal IN−, the bias circuit 64 activates the npn transistor T16 to decrease the output voltage. The activation of the npn transistor T16 is accomplished by increasing the base current of the transistor T16.

The operational amplifier 85a will also be discussed below in terms of (1) restriction on input voltage, (2) restriction on a maximum output voltage, and (3) restriction on a minimum output voltage.

Restriction on Input Voltage

The first input circuit 61, as described above, operates when the input voltages are high, while the second input circuit 62 operates when the input voltages are low. Therefore, the operational amplifier 85a operates normally over an input voltage range of 0 to 5 V (i.e., ground potential to Vcc of 5 V) without any restrictions.

Restriction on Maximum Output Voltage

The transistor T15 disposed in an output stage of the operational amplifier 85a is implemented with a pnp transistor and activated by the bias circuit 64 in response to the voltage lower than the source voltage Vcc by the base-emitter voltage VF5 thereof. A maximum voltage of output from the operational amplifier 85a, thus, drops from the source voltage Vcc by the collector emitter voltage VCE5 of the transistor T15 (i.e., Vcc−VCE5). If VCE5=0.5 V (a load current=22 mA), then the maximum output voltage is restricted to 5 V−0.5 V=4.5 V.

Restriction on Minimum Output Voltage

The transistor T16 is implemented with an npn transistor and activated by the bias circuit 64 in response to the voltage higher than the ground potential by the base-emitter voltage VF6 thereof. A minimum voltage of output from the operational amplifier 85a is, thus, elevated from the ground potential by the collector emitter voltage VCE6 of the transistor T16. If VCE6=0.38 V (a load current=22 mA), then the minimum output voltage is restricted to 0+0.38 V=0.38 V.

Therefore, the output voltage of the operational amplifier 14a operating on 5 V falls within a range of 0.38 to 4.5 V.

Taking use of the operational amplifiers 85a and 86a, as shown in FIG. 1, as voltage followers operating on 5 V into consideration, an input voltage range is, as described above, 0 to 5 V and an output voltage range is 0.38 to 4.5 V, so that an operating voltage range of the operational amplifiers 85a and 86a will be 0.38 to 4.5 V which is wider than that in a conventional air-fuel ratio measuring device such as the one shown in FIG. 1. This results in an increase in accuracy in measuring the A/F ratio.

The source voltage applied to the operational amplifiers 85a and 86a may alternatively be the battery voltage VB of 12 V similar to the first embodiment. In this case, the input and output voltages of each of the operational amplifiers 85a and 86a are restricted as follows. The pnp transistor T15 drops the battery voltage BV by the collector emitter voltage VCE5. A maximum output voltage will, thus, be VB−VCE5. If VCE5=0.5 V, the maximum output voltage is 12 V−0.5 V=11.5 V. The minimum output voltages remains unchanged, 0.38 V. It is, however, necessary for an actual output voltage of the operational amplifiers 85a and 86a used in the air-fuel ratio measuring device to be restricted to below 5 V since the A/D converter 41 operates within a voltage range of 0 to 5 V. An actual operating voltage range of the operational amplifiers 85a and 86a is, therefore, restricted to within 0.38 to 5 V, but it is wider than that in the above second embodiment in which the operational amplifiers 85a and 86a operate on 5 V (Vcc).

In the above modification, the pnp transistor T15 may be replaced with an npn transistor because a voltage drop developed across the base and emitter of the npn transistor falls within a difference between the upper limit (5 V) of the operating voltage range of the operational amplifiers 85a and 86a used in the air-fuel ratio measuring device and the maximum output voltage (11.5 V) thereof. The operational amplifiers 14a and 16a in the first embodiment, as described above, operate only on the battery voltage VB and have the operating voltage range whose lower limit is the ground potential (i.e., 0 V) plus 0.38 V, however, the lower limit may fall within a range of the ground potential to +0.6 V because this operating voltage range also ensures a wider range of voltage applied to the A/F sensor 30 than that in the convention system shown in FIGS. 1 and 2.

Similarly, the operating voltage range of each of the operational amplifiers 85a and 86a operating on the voltage Vcc of 5 V in the second embodiment is the ground potential plus 0.38 V to Vcc minus 0.5 V, however, the upper and lower limits of the operating voltage range may be Vcc minus 0.6 V and the ground potential plus 0.6 V, respectively.

The operational amplifiers 14a, 16a, 85a, and 86a of the air-fuel ratio measuring circuits 10 and 80 all have the rail-to-rail structure, however, at least one of the operational amplifiers of each of the air-fuel ratio measuring circuits 10 and 80 (e.g., the operational amplifiers 14a and 85a) may have the rail-to-rail structure because the operational amplifiers 14a and 85a are employed directly in producing the sensor current Ip (i.e., the voltage across the sensor current detecting circuit 15

In the first and second embodiments, all the amplifying circuits of the air-fuel ratio measuring circuits 10 and 80 are designed to have the rail-to-rail structure, however, at least one of the amplifying circuits in each of the air-fuel ratio measuring circuits 10 and 80 may be made up of a rail-to-rail operational amplifier. For example, the amplifying circuits 14 and 85 may be implemented with a rail-to-rail operational amplifier. This is because the operational amplifiers 14a and 85a contribute directly to increase in unit voltage change developed across the sensor current detecting circuits 15 and 88 by the flow of the sensor current Ip used in determining the A/F ratio.

Each of the first and second embodiments uses bipolar transistors, MOS transistors or IGBTs (Insulated Gate Bipolar Transistors) may be employed.

The sensor current detecting circuit 15 has the two resistors 15a and 15b connected in series, but may have three or more transistors connected in series so that a resistor value of the sensor current detecting circuit 15 for producing a voltage signal inputted to the voltage follower 17 through the switching circuit 18 can be changed in multiple levels. Alternatively, the sensor current detecting circuit 15 may consists of a single resistor, similar to the one shown in FIG. 1.

The air-fuel ration measuring device 100 of the first embodiment is designed to change the voltage applied to the A/F sensor 30 through the air-fuel ratio measuring circuit 10, however, the applied voltage may be kept constant. This eliminates the need for the CPU 21, the A/D converter 22, and the D/A converter 23.

In each of the first and second embodiments, the A/F sensor 30 may be made of a cup shaped limiting current air-fuel ratio sensor, however, a laminated air-fuel ratio sensor may be employed.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims. For example, the present invention may be used with gas concentration measuring devices other than the air-fuel ratio measuring device which are capable of measuring the concentration of gases such as NOx, HC, and CO.

What is claimed is:

1. A gas concentration measuring apparatus comprising:
   a gas concentration sensor exposed to a gas, said gas concentration sensor being responsive to application of voltage to produce a current signal indicative of concentration of the gas; and
   a voltage applying circuit including an operational amplifier which operates on a source voltage developed between a first and a second source voltage developed between a first and a second source terminal thereof connected to a voltage source, the operational amplifier outputting voltage for developing the voltage applied to said gas concentration sensor which has a level changing as a function of voltage inputted to the operational amplifier,
   wherein an npn transistor is disposed in an output stage of the operational amplifier, the npn transistor serving as a current sink element and connecting at an emitter with ground and at a collector with an output terminal of the operational amplifier, and the operation amplifier is designed to have an amplitude of each of the voltages inputted to and outputted from the operational amplifier which falls within a given input/output voltage range defined between an upper limit and a lower limit of a source voltage range of the voltage developed by the voltage source between the first and second source terminals of the operational amplifier and the amplitude having a difference of less than or equal to 0.6 V between at least one of the upper and lower limits of the source voltage range.

2. The gas concentration measuring apparatus as set forth in claim 1, wherein the difference is between an upper limit of the input/output voltage range and the upper limit of the source voltage range.

3. The gas concentration measuring apparatus as set forth in claim 1, wherein the difference is between a lower limit of the input/output voltage range and the lower limit of the source voltage range.

4. The gas concentration measuring aaparatus as set forth in claim 1, wherein the differences are between an upper limit of the input/output voltage range and the upper limit of the source voltage range and between a lower limit of the input/output voltage range and the lower limit of the source voltage range respectively.

5. The gas concentration measuring apparatus as set forth in claim 1, wherein said gas concentration sensor measures the concentration of a preselected component of exhaust gasses of an engine mounted in an automotive vehicle, and wherein the first source terminal of the operational amplifier is connected to a positive terminal of a single battery installed in the vehicle, while the second source terminal is kept at a reference potential.

6. The gas concentration measuring apparatus as set forth in claim 1, wherein said gas concentration sensor measures the concentration of a preselected component of exhaust gasses of an engine of an automotive vehicle, wherein the voltage source is a constant voltage source for a digital signal connecting with the first source terminal of the operational amplifier, while the second source terminal is kept at a reference potential, and wherein an upper limit of the input/output voltage range lies between the voltage provided by the constant voltage source and the voltage provided by the constant voltage source minus 0.6 V, while a lower limit of the input/output voltage range lies between a ground potential and the ground potential plus 0.6 V.

7. The gas concentration measuring apparatus as set forth in claim 1, wherein the operational amplifier has a pnp transistor disposed in an output stage thereof, the pnp transistor serving as a current source element and connecting at an emitter with the voltage source and at a collector with an output terminal of the operational amplifier.

8. The gas concentration measuring apparatus as set forth in claim 1, wherein the operational amplifier includes a first input stage to which a higher voltage is inputted and a second input stage to which a lower voltage is inputted.

9. The gas concentration measuring apparatus as set forth in claim 1, wherein the operational amplifier is designed to have a rail-to-rail structure.

10. The gas concentration measuring apparatus as set forth in claim 1, further comprising a resistor circuit which is disposed between an output terminal of the operational amplifier and said gas concentration sensor, a voltage signal outputting circuit which outputs voltage appearing across said resistor circuit changing as a function of the current signal flowing through said gas concentration sensor, and a resistor changing circuit which changes a resistor value of said resistor circuit as a function of a value of the current signal.

11. The gas concentration measuring apparatus as set forth in claim 10, wherein said resistor changing circuit decreases the resistor value of said resistor circuit as the concentration of the gas increases.

12. A gas concentration measuring apparatus as set forth in claim 1, wherein said gas concentration sensor outputs a limit current as a function of the concentration of the gas in response to the application of a given voltage.

13. A gas concentration measuring apparatus comprising:
   a gas concentration sensor exposed to a gas, said gas concentration sensor producing a current signal indicative of concentration of the gas when input voltage is developed across a first and a second terminal of the gas concentration sensor;
   a first operational amplifier operating on a source voltage developed between a first and a second source terminal thereof connected to a voltage source, said first operational amplifier outputting voltage to develop a first electric potentioal at the first terminal of said gas concentration sensor, the voltage outputted from said first operational amplifier changing as a function of voltage inputted to said first operational amplifier; and
   a second operational amplifier operating on the source voltage developed between a first and a second source terminal thereof connected to the voltage source; said second operational amplifier outputting voltage to develop a second electric potential at the second terminal of said gas concentration sensor for creating the input voltage applied to said gas concentration sensor, the voltage outputted from said second operational amplifier changing as a function of voltage inputted to said second operational amplifier,
   wherein each of said first and second operational amplifiers is designed to have an amplitude of each of the voltages inputted thereto and outputted therefrom which falls within a given input/output voltage range defined between an upper limit and a lower limit of a source voltage range of the voltage developed by the voltage source between the first and second source terminals of one of said first and second operational amplifiers and each of the amplitudes having a difference of less than or equal to 0.6 V between at least one of the upper and lower limits of the source voltage range.

* * * * *